United States Patent

Vogt

(10) Patent No.: US 9,901,953 B2
(45) Date of Patent: Feb. 27, 2018

(54) PASTE APPLICATION DEVICE FOR THE MIXING OF A PASTE FROM TWO COMPONENTS

(71) Applicant: Heraeus Medical GmbH, Wehrheim (DE)

(72) Inventor: Sebastian Vogt, Erfurt (DE)

(73) Assignee: Heraeus Medical GmbH, Wehrheim (DE)

( * ) Notice: Subject to any disclaimer, the term of this patent is extended or adjusted under 35 U.S.C. 154(b) by 50 days.

(21) Appl. No.: 15/006,710

(22) Filed: Jan. 26, 2016

(65) Prior Publication Data

US 2016/0214135 A1 Jul. 28, 2016

(30) Foreign Application Priority Data

Jan. 27, 2015 (DE) .................. 10 2015 101 126

(51) Int. Cl.
*B67D 7/70* (2010.01)
*B05C 17/005* (2006.01)
(Continued)

(52) U.S. Cl.
CPC .... *B05C 17/00553* (2013.01); *A61B 17/8816* (2013.01); *A61B 17/8822* (2013.01);
(Continued)

(58) Field of Classification Search
CPC .......... B05C 17/00553; B05C 17/0146; B05C 17/015; B05C 17/00559; B05C 17/00503;
(Continued)

(56) References Cited

U.S. PATENT DOCUMENTS 2,818,999 A 1/1958 Miller
2,943,768 A 7/1960 Lindsay
(Continued)

FOREIGN PATENT DOCUMENTS

DE 102007052116 A1 4/2009
DE 102007050762 B3 5/2009
(Continued)

OTHER PUBLICATIONS

Japanese Office Action for corresponding Japanese Application No. 2016-006787 dated Jan. 24, 2017.
(Continued)

*Primary Examiner* — J. Casimer Jacyna
(74) *Attorney, Agent, or Firm* — Norris McLaughlin & Marcus, P.A.

(57) ABSTRACT

A paste application device stores two starting components, for mixing the starting components to form a paste and for the application of the paste. The comprises a two-component cartridge comprising two cylindrical internal spaces, two feed plungers that can be shifted axially in the internal spaces and limit the internal spaces on a first side of the two-component cartridge, and at least two dispensing openings by means of which the internal spaces are open on a second side of the two-component cartridge that is opposite from the first side, a hollow cylinder that is made of a plastic material and has one front face that is open and one front face that is partially closed, in which is situated an axially mobile plunger that has two pestles attached to it, whereby the pestles are oriented in the direction of the open front face, whereby the open front face of the hollow cylinder is arranged to axially touch against the first side of the two-component cartridge, and whereby the plunger closes in gas-tight manner against the internal walls of the hollow cylinder, whereby the two-component cartridge and the
(Continued)

hollow cylinder are arranged in a pressure vessel, whereby the pressure vessel touches against the hollow cylinder or is situated at a distance from the hollow cylinder of at most 0.1 mm.

19 Claims, 8 Drawing Sheets

(51) Int. Cl.
  *B05C 17/015* (2006.01)
  *B05C 17/01* (2006.01)
  *A61B 17/88* (2006.01)

(52) U.S. Cl.
  CPC ...... *B05C 17/00559* (2013.01); *B05C 17/015* (2013.01); *B05C 17/0146* (2013.01); *A61B 2017/8838* (2013.01); *B05C 17/00503* (2013.01); *B05C 17/00513* (2013.01); *B05C 17/00576* (2013.01)

(58) Field of Classification Search
  CPC ........ B05C 17/00576; B05C 17/00513; B05C 17/00573; A61B 17/8822; A61B 17/8816; A61B 2017/8838
  See application file for complete search history.

(56) References Cited

U.S. PATENT DOCUMENTS

| | | | |
|---|---|---|---|
| 3,767,085 A | | 10/1973 | Cannon et al. |
| 4,067,479 A | | 1/1978 | Moline |
| 4,366,919 A | | 1/1983 | Anderson |
| 4,690,306 A | | 9/1987 | Stäeheli |
| 4,925,061 A | | 5/1990 | Jeromson, Jr. et al. |
| 5,477,987 A | * | 12/1995 | Keller ............... B05C 17/00513 222/137 |
| 5,566,860 A | * | 10/1996 | Schiltz ............. B05C 17/00513 222/105 |
| 5,647,510 A | | 7/1997 | Keller |
| 5,893,486 A | * | 4/1999 | Wasmire .......... B05C 17/00513 222/190 |
| 6,935,541 B1 | * | 8/2005 | Campbell ............. B05C 17/015 137/557 |
| 8,986,313 B2 | | 3/2015 | Vogt et al. |
| 2004/0056045 A1 | | 3/2004 | Kosmyna et al. |
| 2004/0074927 A1 | | 4/2004 | Lafond |
| 2006/0043119 A1 | | 3/2006 | Gibbons et al. |
| 2006/0191962 A1 | * | 8/2006 | Redl ................. A61B 17/00491 222/386 |
| 2008/0086079 A1 | | 4/2008 | Williamson et al. |
| 2008/0208114 A1 | | 8/2008 | Landau et al. |
| 2009/0105144 A1 | | 4/2009 | Vogt et al. |
| 2009/0105366 A1 | | 4/2009 | Vogt et al. |
| 2011/0084094 A1 | | 4/2011 | Reidt et al. |
| 2011/0272433 A1 | | 11/2011 | Vogt et al. |
| 2017/0128113 A1 | * | 5/2017 | Vogt ................... A61B 17/8819 |

FOREIGN PATENT DOCUMENTS

| | | |
|---|---|---|
| DE | 102008030312 A1 | 1/2010 |
| DE | 102010019223 A1 | 11/2011 |
| EP | 1118313 B1 | 2/2005 |
| JP | S62-096821 A | 5/1987 |
| JP | H08-502712 A | 3/1996 |
| JP | 2014237006 A | 12/2014 |
| TW | I265829 B | 11/2006 |
| WO | 2005/084819 A2 | 9/2005 |

OTHER PUBLICATIONS

Kuehn, Klaus-Dieter; "Knochenzemente fuer die Endoprothetik"; Springer-Verlag, 2000, pp. 18-19, Springer-Verlag of BertelmannSpringer publishing group, Berlin, Germany.

Australian Office Action corresponding to Australian Patent Application No. 2016200109 dated Sep. 27, 2016.

Taiwan Office Action corresponding to Taiwanese Patent Application No. 105100974 dated Sep. 5, 2016.

\* cited by examiner

PASTE APPLICATION DEVICE FOR THE MIXING OF A PASTE FROM TWO COMPONENTS

FIELD OF THE DISCLOSURE

The invention relates to a paste application device for storage of two starting components, for mixing the starting components to form a paste, and for application of the paste.

The invention further relates to a method for mixing and dispensing a paste.

Accordingly, the object of the invention is a manually operable paste application device designed for dispensing pasty masses, in particular pasty polymethylmethacrylate cement dough (PMMA cement dough). The paste application device and the method are further intended for storing, mixing, and dispensing pasty two-component systems.

BACKGROUND OF THE DISCLOSURE

Conventional polymethylmethacrylate bone cements (PMMA bone cements) are usually made from a powdered component and a liquid monomer component (K.-D. Kühn: Knochenzemente für die Endoprothetik: ein aktueller Vergleich der physikalischen and chemischen Eigenschaften handelsublicher PMMA-Zemente. Springer-Verlag Berlin Heidelberg New York, 2001). After mixing the cement powder with the liquid monomer component, said PMMA bone cements are applied in their non-cured pasty state in the form of a cement dough. If mixing systems are used with powder-liquid cements, the cement dough is situated in a cartridge. The cement dough is squeezed from said cartridge through the motion of a feed plunger. A motion of the feed plunger of this type can be effected by means of a mechanical application device.

In the case of pasty two-component pastes and/or two component bone cements, such as are known, for example, from DE 10 2007 050 762 B3, DE 10 2008 030 312 A1 or DE 10 2007 052 116 B4, both pasty components are stored in two separate cartridges with two separate feed plungers. During application, both pastes are pressed from the interior spaces of the cartridge into a static mixer through the motion of the feed plungers and are dispensed through a dispensing tube once the mixing is completed.

The application of pasty adhesives and sealants is done basically the same way using paste application devices.

Currently, paste application devices that can be driven manually or pneumatically or electrically are used to extrude thick viscous masses. Customary simple mechanical paste application devices utilise, in particular, clamp rods that are driven by a manually-operated tilting lever for extrusion. In the case of highly viscous pastes, said devices can be operated only by exerting very strong forces. This exertion of force is unreasonable for medical users in the OR.

Electrically-driven extrusion devices can be driven both with rechargeable batteries and/or batteries or by means of a stationary electrical power supply. Said devices can extrude particularly thick pasty masses since their force is very large in some cases. However, it is one disadvantage of the use of electrical motors that these motors contain non-ferrous metals and are expensive. Moreover, rechargeable batteries must be kept in stock or a cable connection, which is an impediment in the OR area, must be provided by means of which the paste application device must be connected to a power network.

Pneumatic paste application systems, like the systems known, for example, from U.S. Pat. No. 2,004,074 927 A1 or U.S. Pat. No. 6,935,541 B, require a compressed air connection. This necessitates compressed air hoses, which may impede the mobility of the user and the use of the paste application system. Alternatively, the use of compressed gas cartridges to provide compressed gas is feasible just as well. Documents U.S. Pat. No. 2,818,999 A and EP 1 118 313 A1 shall be cited as being exemplary in this context.

An interesting proposal is described in EP 4 925 061 A1. This system has no gas cartridge arranged in the device. The device needs to be filled with compressed gas by means of a valve prior to its application. Aid device contains a cartridge, in which the viscous mass is arranged. A plunger that is connected to one end of the cartridge by means of a bellows is arranged behind the viscous mass. Before application, a liquid gas is filled through a valve into the hollow space formed by the plunger, the bellows, and the cartridge end. This proposal has to be seen in a critical light, since the expansion of liquid gas is associated with cooling which may lead to the elastic bellows becoming brittle. If the bellows becomes brittle, leakiness cannot be excluded. As a result, compressed gas can exit through the bellows and penetrate into the viscous mass adjacent to the plunger. Any mixing of the pastes with compressed gas is inacceptable in the case of polymethylmethacrylate bone cement pastes. Gas bubbles would weaken the cured polymethylmethacrylate. Moreover, the liquid compressed gas is difficult to fill into the receptacle and it is unreasonable to expect users in the OR to do this.

DE 10 2010 019 223 B4 proposed a cementing device, in which a compressed gas cartridge is punctured by means of the motion of a rotary valve. The compressed gas presses directly onto the plunger of the device. The dispensation of the pastes is regulated by a valve. It is a advantage of said device that high-strength plastic materials need to be used for the cartridges, since no pressure vessel is provided.

Basically, it is feasible with all compressed gas-driven paste application devices having feed plungers that the compressed gas passes by the feed plunger into the pastes in unwanted manner. This issue may be more pronounced the higher the gas pressure is.

Moreover, devices for the dispensation of medications are known from the field of medicine that also utilise compressed gas cartridges as energy source, although no regulation of the volume flow of the medication by means of valves is provided (U.S. Pat. No. 2,008,086 079 A1, U.S. Pat. No. 2,008,208 114 A1). Systems of this type are not very useful for bone cements, since they do not allow for specific portioning of the bone cement dough during the operation.

SUMMARY OF THE DISCLOSURE

It is the object of the invention to overcome the disadvantages of the prior art. Specifically, a paste application device and a method for mixing and dispensing of the paste are to be found by means of which even very viscous starting components can be stored, mixed, and dispensed using a simple design. In this context, the paste application system shall be sufficiently inexpensive to enable its single use (disposable article). Disposable articles are particularly advantageous in surgical theatres due to the existing strict hygienic requirements.

It is the object of the invention to overcome the disadvantages of the previously known paste application devices for storing, mixing and applying pasty polymethylmethacrylate bone cements, in which the energy for mixing and applying is provided by a compressed gas cartridge that is integrated into the device.

Moreover, one object of the invention is to provide a paste application device that can be driven without the use of external stationary energy sources, such as compressed air or electrical current, and that is capable of extruding and mixing viscous pasty masses. In addition, the paste application device shall contain no copper and no copper alloys. Moreover, it shall be feasible for the user to use it independent of location and it shall have a maximally simplified structure. By this means, it shall be feasible to provide an inexpensive paste application device that is intended for single use only. Moreover, it is another object of the invention to develop a method for the dispensing of pasty masses by means of the paste application device to be developed.

Moreover, it shall be feasible to store two cement pastes separately in the paste application device before applying the cement. Moreover, it must be feasible to sterilise the surface of the paste application device with ethylene oxide. It is important that the high-pressure required during the application does not lead to undesired leakage of cement, which might lead to contamination of the medical user and surgical theatre (OR room). It should be possible to manually operate the paste application device with as little force as possible. Another important point for application is that no substantial amounts of the cement dough and/or paste continue to flow out when the operation of the paste application device is stopped.

Moreover, a device that is suitable for storing, mixing, and dispensing highly viscous pasty polymethylmethacrylate bone cement is to be developed, whereby compressed gas that is stored in a compressed gas cartridge that is integrated into the paste application device is to be used as the energy source. It is another object of the invention to provide for the paste application device to safely tolerate, mechanically, high gas pressures in excess of 30 bar over an application period of a few minutes without the paste application device becoming deformed or destroyed. Moreover, the production of the paste application device to be developed shall be inexpensive. Moreover, the paste application device should contain no compressed gas flow-regulating valves and no separate devices intended for evaporation of liquid compressed gas. The paste application device to be developed shall be robust enough in structures such that the compressed gas can be present as a mixture containing liquid compressed gas. If liquid carbon dioxide is used as compressed gas, the paste application device must also tolerate mixtures of gaseous, liquid, and solid carbon dioxide without mechanical damage or deformation.

The objects of the invention are met by a paste application device for storing two starting components, for mixing the starting components to form a paste, and for application of the paste, comprising
a two-component cartridge comprising two cylindrical internal spaces, two feed plungers that can be shifted axially in the internal spaces and limit the internal spaces on a first side of the two-component cartridge, and at least two dispensing openings by means of which the internal spaces are open on a second side of the two-component cartridge that is opposite from the first side,
a hollow cylinder that is made of a plastic material and has one front face that is open and one front face that is partially closed, in which is situated an axially mobile plunger that has two pestles attached to it, whereby the pestles are oriented in the direction of the open front face, whereby the open front face of the hollow cylinder is arranged to axially touch against the first side of the two-component cartridge, and whereby the plunger closes in gas-tight manner against the internal walls of the hollow cylinder,
whereby the two-component cartridge and the hollow cylinder are arranged in a pressure vessel made of metal, a high-strength plastic material or a fibre-reinforced plastic material, whereby the pressure vessel touches against the hollow cylinder or is situated at a distance from the hollow cylinder of at most 0.1 mm,
whereby the hollow cylinder comprises, on the front face that is partially closed, a connector for a compressed gas cartridge that extends through an opening in the pressure vessel, and whereby a manually operable valve element is attached downstream from the dispensing openings or a dispensing tube having a manually operable valve element can be attached downstream from the dispensing openings, whereby the valve element attached downstream from the dispensing openings can be used to regulate the volume flow of the starting components through the dispensing openings.

Being able to regulate the volume flow of the starting components through the dispensing openings means, in particular, that the volume flow can be stopped by closing the valve element.

According to the invention, a cylinder geometry shall be understood to be the general cylinder shape with any footprint and therefore not only cylinders with a circular footprint.

The internal spaces are preferably filled with two starting components, which are to be mixed and of which at least one is a paste, whereby the mixed starting components particularly preferably form a PMMA bone cement. It shall be feasible to apply the mixture with the paste application device.

Preferably, the plunger closes against the internal walls of the hollow cylinder not only in gas-tight manner, but even in pressure-tight manner up to at least 10 atmospheres and/or up to at least 1,000 kPa, particularly preferably in pressure-tight manner up to at least 3,000 kPa.

The pressure vessel can receive the pressure forces even if there is a small distance of maximally 0.1 mm between the pressure vessel in the hollow cylinder, since the relaxation of the gas from the compressed gas cartridge that occurs when the compressed gas is conducted from the compressed gas cartridge into the hollow cylinder is associated with an expansion (partial adiabatic expansion), during which the relaxing gas cools down, which in turn cools the surrounding containers and, as a result, the hollow cylinder made of plastic material contracts less strongly than the pressure vessel, if the latter is made of metal or metal alloy, and, as a result, the metallic pressure vessel touches against the hollow cylinder.

Metals or metal alloys are preferred as material for the pressure vessel, since many metallic materials are easy to process despite their high compressive strength and/or despite their high tensile strength. Conceivable high-strength plastic materials for the pressure vessel include duroplasts, polyamides, polyamide-co-imides, polysulfones, polyketones, and polyetherketones, although these are more difficult to process than metals or metal alloys and are therefore less preferred as material for the pressure vessel. Glass fibre-reinforced plastic materials are particularly preferred as fibre-reinforced plastics.

Moreover, the valve element is preferably arranged outside of the pressure vessel. According to the invention, the axle of the valve element preferably consists of steel in order to be able to receive the forces acting on the flap without deformation or destruction.

Paste application devices according to the invention can also be provided such that the valve element is arranged in a conduit that is formed by a dispensing tube, whereby it is preferred to have, in addition, a static mixture provided in the dispensing tube by means of which the starting components can be mixed while flowing through the mixer.

This allows for a particularly simple design to be attained that can be implemented inexpensively and at the same time is insensitive to failure and is sufficiently stable for the regulation of high-pressure flows of the starting components.

Moreover, the invention can provide the pressure vessel to have a two-part design, whereby the two parts are connected to each other in force-locking manner by riveting, by a screw connection and/or by a union nut, whereby a first part of the two parts of the pressure vessel preferably contains the two-component cartridge and the second of the two parts of the pressure vessel (i.e. the other part of the pressure vessel) contains the hollow cylinder.

This simplifies the production and assembly of the paste application device. In particular, filling the two-component cartridge with the starting components is simplified clearly by this means. Preferably, the two parts of the pressure vessel are connected to each other in a form-fit and/or material-bonded manner.

Preferred embodiments of the invention can be characterised in that the two-component cartridge, or at least regions thereof, is a coaxial cartridge, whereby one of the internal spaces in the coaxial cartridge is cylindrical and situated inside and the other internal space is cylindrical and coaxially surrounds the inner internal space.

The feed plungers are adapted to match the internal shape of the cylindrical internal spaces. The cylinder shape is advantageous because the strong forces occurring during the extrusion of the starting components and/or during the application of the pressure from the compressed gas cartridge to the two-component cartridge can be received uniformly by the pressure vessel. Moreover, it is feasible to manufacture components with cylindrical geometry inexpensively.

Moreover, the invention can provide the paste application device to comprise a closure for closing the dispensing openings that can be fastened by means of a fastening means of the closure, in particular by means of a thread of the closure, to an opposite fastening means in the region of the dispensing openings, in particular to an opposite thread in the region of the dispensing openings, whereby it is preferred that the dispensing tube, which also comprises a corresponding fastening means for this purpose, can be fastened to the opposite fastening means.

As a result, the starting components can be stored in the paste application device for a longer period of time, since the closure affords a better and more air-tight closure of the internal spaces containing the starting components as compared to only the valve element sealing the internal spaces.

In this context, the invention can provide the closure to be a key for opening the compressed gas cartridge and/or for connecting the compressed gas cartridge to the connector of the hollow cylinder, whereby the closure preferably can be plugged, on the floor-side, onto the compressed gas cartridge as a key thus rendering the compressed gas cartridge movable, in particular rotatable and/or shiftable in longitudinal direction, for opening the compressed gas cartridge and/or for connecting the compressed gas cartridge to the connector of the hollow cylinder.

As a result, premature inadvertent opening of the compressed gas cartridge can be prevented such that the operation of the paste application device is simplified.

Preferably, the invention can just as well provide a compressed gas cartridge fastening means on the connector of the hollow cylinder by means of which the compressed gas cartridge can be attached to the connector in pressure-tight manner, and/or provide a puncturing mandrel for opening of the compressed gas cartridge on the connector of the hollow cylinder.

This design attains a secure and tight connection and/or prevents premature inadvertent opening of the compressed gas cartridge. The compressed gas cartridge fastening means is preferably an internal thread into which an external thread of the compressed gas cartridge can be screwed. Moreover, a gasket (for example in the form of an O ring) can be provided on a connecting surface and allows better sealing of the connection of the compressed gas cartridge to the hollow cylinder to be attained.

In order to improve the storage properties, the invention can provide a protective foil/film to be arranged between the hollow cylinder and the two-component cartridge and the protective foil/film to close the internal spaces of the two-component cartridge on the first side, whereby the protective foil/film preferably is pasted, welded or bonded onto the two-component cartridge.

Improved sealing of the internal space can be attained by means of the protective foil/film such that longer and/or quality-preserving storage of starting components with volatile ingredients, such as methylmethacrylate, in the internal spaces is made feasible. In operation, the protective foil/film is punctured when the pestles are propelled through the plunger in the hollow cylinder, such that the pestles can propel the feed plungers in the two-component cartridge and thus can extrude the starting components from the two-component cartridge through the dispensing openings from the internal spaces of the two-component cartridge.

The protective foil/film is preferred to be an aluminium composite foil. Aluminium and/or aluminium-coated foils are particularly tight with respect to methylmethacrylate vapours such that the paste application device is then particularly well-suited for storage of the starting components of a PMMA bone cement.

Preferred paste application devices can provide the pressure vessel to consist of aluminium, zinc, an aluminium alloy or steel.

Attendant forces can be received particularly well by the pressure vessel made of these materials without the pressure vessel being destroyed. Moreover, these metallic materials are easy to shape as desired during the production process.

According to the invention, it can be preferred to provide the pressure vessel to have a tensile modulus in accordance with EN ISO 527 in excess of 1,500 MPa.

It can also be preferred according to the invention that the pressure vessel has a compressive strength of at least 3 MPa.

The invention can just as well provide the pressure vessel to comprise a cylindrical internal space for accommodation of the hollow cylinder and the two-component cartridge. The cylindrical geometry is particularly well-suited for receiving the forces and is easy to generate during production.

Particularly advantageous embodiments of the present invention can provide the manually operable valve element to be operable from outside by means of an operating element, preferably to be operable by means of a lever on the dispensing tube or a trigger on a handle of the paste application device.

By this means, the paste application device is easy to operate from outside and is therefore a user-friendly. Preferably, the valve element in the dispensing tube can be operable from outside, whereby the valve element particularly preferably is opened and closed by means of a manually triggered rotary motion. The invention can just as well provide a closure part of the valve element to be connected to a lever that is arranged on the outside of the paste application device such as to be parallel to the longitudinal axis, whereby the lever is moved manually to open and close the valve element such that the closure part rotates in the valve seat. Moreover, the invention can provide the closure part to be connected in force-locked or form-fitting manner to a manual triggering device that is arranged parallel to the longitudinal axis of the paste application device, whereby, upon a manual linear motion of the triggering device parallel to the longitudinal axis or upon a manual tilting motion of the triggering device proceeding tangentially to the longitudinal axis, the motion is transferred by means of a gear, in particular a linkage, into an at least partial rotary motion of the closure part of the valve element. A paste application device with triggering device can also be provided such that the closure part of the valve element is connected to a first lever, whereby a lever end is designed as a first inclined plane with an angle of 20° to 45° and, opposite to said first inclined plane, a second inclined plane of a second lever is arranged and is connected to a manually operable trigger, whereby both inclined planes that are arranged opposite from each other engage each other appropriately such that, upon a linear motion of the second lever by means of the trigger, the second inclined plane and the first inclined plane jointly with the first lever swivel by at least 5° from the longitudinal axis of the device, whereby the closure part is rotated in the valve seat by the swiveling motion of the first lever. In this context, the invention can, in turn, provide an elastic restoring element to be arranged on the first lever by means of which the first lever is pushed back into its starting position after the swiveling motion of the first lever caused by the linear motion of the second inclined plane and/or an elastic restoring element to be arranged on the second lever that pushes the second lever back into the starting position after a manual linear motion proceeded.

Preferably, the valve element is designed as a cylinder-shaped rotary valve, as a ball valve or as a flap well, whereby the flap valve is particularly preferred.

A refinement proposes to provide in the external wall of the hollow cylinder, namely in the half facing in the direction of the two-component cartridge, and in the wall of the pressure vessel at least one through-going ventilation opening such that the pressure escapes from the hollow cylinder when the plunger is arranged between (axially between) the ventilation opening and the two-component cartridge.

As a result, the paste application device is rendered free of pressure after extrusion of the starting components and can subsequently be recycled or disposed of without any danger. The ventilation openings connect the space between the two-component cartridge and the axially mobile pestles in the hollow cylinder to the surrounding atmosphere in gas-permeable manner. In this context, the invention can provide the compressed gas to escape into the surroundings when the plunger reaches the end-position in the hollow cylinder.

Preferably, the at least one ventilation opening of the hollow cylinder is arranged in the cylinder jacket wall of the hollow cylinder. Also preferably, the at least one ventilation opening of the pressure vessel is arranged in the cylinder jacket wall of the pressure vessel. It can be particularly preferably to also provide the ventilation openings in the hollow cylinder and in the pressure vessel to be arranged such as to overlap with each other. A manually operable valve element for releasing the compressed air can be arranged on the at least one ventilation opening of the pressure vessel.

According to a refinement, the invention can provide the two-component cartridge, the hollow cylinder, and the pressure vessel to be arranged in a housing, whereby it is preferred for the pressure gas cartridge to also be arranged in the housing.

As a result, the paste application device is being closed towards the outside. The housing preferably consists of plastic material.

Preferably, the invention can provide the distances between the pressure vessel and the external wall of the two-component cartridge and between the pressure vessel and the external wall of the hollow cylinder to be smaller than 100 μm, preferably to be smaller than 50 μm.

As a result, the pressure vessel of the paste application device can receive the pressure without major deformation of the hollow cylinder and of the two-component cartridge. The external wall of the two-component cartridge preferably consists of plastic material. The feed plungers can also be made from plastic material, whereby it is preferred, in addition, to arrange on the feed plungers circumferential gaskets for sealing the feed plungers with respect to the internal spaces. Moreover, wiper lips can be arranged on the feed plungers by means of which the content of the internal spaces can be expelled from the internal spaces either completely or at least 99% thereof.

Moreover, the invention can provide that the paste application device can be held by one hand and that the valve element can be operated by the same hand. As a result, the use of the paste application device is made simpler.

The objects underlying the present invention are also solved through a method for mixing and expelling a paste comprising the steps of:

conducting a compressed gas from the compressed gas cartridge through the connector of the hollow cylinder into the hollow cylinder, whereby the pressure vessel receives the force of the compressed gas acting on the walls of the hollow cylinder and the plunger with the pestles is propelled by the compressed gas in the hollow cylinder in the direction of the two-component cartridge;

the propelled pestles of the plunger drive the feed plungers forward into the at least two internal spaces of the two-component cartridge, whereby the starting components are expelled from the internal spaces of the two-component cartridge through the at least two dispensing openings of the internal spaces;

whereby the flow of the starting components is stopped by a closed valve element downstream of the dispensing openings as seen in flow direction and a manual operation of an operating element opens the valve element, such that the starting components and/or the mixture thereof flow through the valve element and, after the starting components are mixed, the mixture is being applied.

In this context, the invention can provide the forces, which occur when the liquid is compressed gas is conducted into the hollow cylinder and when the plunger and the feed plunger are propelled in the two-component cartridge, to be taken up by the pressure vessel, in particular by an essentially cylindrical pressure vessel, that surrounds the two-component cartridge and the hollow cylinder, whereby the pressure vessel particularly preferably touches against the two-component cartridge and the hollow cylinder.

Preferably, the invention provides for the use of a paste application device according to the invention for implementation of the method.

Moreover, in the absence of a manual force acting on the operating element, the invention can provide for the valve element to be closed by the action of a force of a restoring element, in particular of an elastic spring.

Finally, the method also proposes a closure to be removed from the paste application device before conducting the compressed gas into it, and the closure to close the dispensing openings of the internal spaces of the two-component cartridge, and a dispensing tube to be attached in front of the dispensing openings of the internal spaces, in which the valve element is arranged. In this context, the invention can preferably provide the compressed gas cartridge to be opened after attaching the dispensing tube. In turn, the invention can particularly preferably provide the compressed gas to be conducted into the hollow cylinder upon the compressed gas cartridge being opened.

The invention is based on finding, surprisingly, that, using a pressure vessel and a valve element that is arranged downstream of the cartridges (downstream of the internal spaces of the two-component cartridge) and is filled with viscous starting components, it is feasible to generate a direct drive of the feed plungers by means of the gas pressure from a compressed gas cartridge without first having to reduce the pressure of the gas. The pressure vessel is capable of receiving the strong attendant forces without the plastic form bodies (the two-component cartridge and the hollow cylinder), which are situated inside, becoming deformed or becoming deformed too strongly. The plastic form bodies, which are situated inside, should be made from plastic material such that the drive elements (the plunger and the feed plungers) slide well in the plastic form bodies and, at the same time, have a sealing effect. For this purpose, the valve element must be designed to be sufficiently stable. The positioning in a relatively narrow channel downstream of the internal spaces of the two-component cartridge helps to design the structure of the valve element stable enough without any major design effort. Theoretically, the valve element can just as well be arranged downstream of a static mixture, which then further reduces the force acting on the valve element. As a result, the design can be made to be relatively simple and functional without requiring sophisticated components for conducting and impacting the flow of compressed gas. Reducing the number of components also reduces the sensitivity of the paste application device to malfunction or interference significantly.

Own experiments with compressed gas-driven paste application devices have shown that it is essential that the components exposed to compressed gas are gas-tight and do not strongly deform due to the pressure to the extent that the function of the paste application device would be impaired. In further experiments, it was found that it is very difficult to store cement cartridges appropriately during the dispensation of the cement pastes, during the propulsion of the feed plungers by pestles, such that the cement cartridges do not move away from the pestles and the pestle drive due to deformation or twisting at internal pressures in excess of 20 bar. Own experiments further showed that cement cartridges made of aluminium alloys are unsuitable for polymethylmethacrylate cement pastes, since the alloys and the alloy ingredients present in them, such as copper and manganese, effect an undesired radical polymerisation during the storage of cement pastes in the cement cartridge and/or in the internal spaces. Polymethylmethacrylate-containing cement pastes are sufficiently long-term stable on storage only in cement cartridges made from suitable plastic materials, such as poly-acrylonitrile-co-methylmethacrylate and polybutylene terephthalate.

A first, very general exemplary embodiment of the invention shall be described in the following:

An exemplary paste application device is composed of a) a hollow cylinder-shaped first pressure vessel having a minimal compressive strength of 30 bar;

b) at at least one plastic cartridge that has an axially mobile dispensing plunger and is arranged in the first pressure vessel;

c) a dispensing tube that contains a static mixture and a valve element and is connected to the plastic cartridge in form-fitting manner, whereby the valve element is arranged outside of the first pressure vessel;

d) a plastic hollow cylinder having one open and one closed front face, whereby a hollow cylinder is arranged on the outside of the plastic hollow cylinder and is connected to the internal space of the plastic hollow cylinder in gas-permeable manner and has an external thread on its outside;

e) a hollow cylinder-shaped second pressure vessel that has a minimal compressive strength of 30 bar, an open front face, and a closed front face, whereby the closed front face has a perforation, whereby f) the plastic hollow cylinder is arranged appropriately in the second pressure vessel such that the hollow cylinder projects through the perforation of the second pressure vessel;

g) the gap between the plastic hollow cylinder and the second pressure vessel is smaller than 0.1 mm;

h) an axially mobile plunger (drive plunger) is arranged in the plastic hollow cylinder, whereby the plunger is connected to at least one pestle;

i) an opening device for a gas cartridge is arranged outside of the pressure vessel and is screwed connected to the hollow cylinder by means of an internal thread;

j) the two pressure vessels being connected to each other in form-fitting or material-bonded manner; and k) a closed housing, in which the first pressure vessel, the second pressure vessel, the opening device of the gas cartridge, and the gas cartridge are arranged.

The pressure vessel and/or the pressure vessels are preferably made of metal and/or of plastic material and/or of glass fibre-reinforced plastic material. Particularly preferably, the pressure vessels consist of metal. Aluminium alloys, steel or zinc are particularly preferred in this context. The pressure vessel and can be produced by impact extrusion, pressure die-casting or mechanical processing methods. It is particularly advantageous to produce pressure vessels from aluminium alloys by impact extrusion.

According to the invention, the hollow body with the drive plunger possesses at least one gas-permeable opening that is connected to at least one gas-permeable opening of the second pressure vessel in gas-permeable manner, whereby the gas-permeable opening of the hollow body is arranged appropriately such that the compressed gas escapes into the surroundings when the drive plunger reaches the end-position. As a result, the device becomes unpressurised after complete dispensation of the cement pastes and thus secures itself. The unpressurised device can be disposed of without any problems.

According to the invention, the valve element in the dispensing tube can be actuated from outside, whereby the valve element preferably is opened and closed through a manually triggered rotary motion, whereby the valve element particularly preferably is designed to be a cylinder-shaped rotary valve, a ball valve or a flap valve, and whereby the flap valve is particularly preferred.

It is advantageous to have the closure part of the valve element be connected to a lever that is arranged on the outside of the housing such as to be parallel to the longitudinal axis, whereby the lever is moved manually to open and close the valve element such that the closure part rotates in the valve seat. As a result, the medical user can regulate the dispensation of the mixed cement dough without any problem.

In a further refinement of the invention, the closure part is connected in force-locked or form-fitting manner to a manual triggering device that is arranged such as to be parallel to the longitudinal axis of the device, whereby the linear motion resulting from linearly moving the triggering device parallel to the longitudinal axis by hand is converted by means of a gear into an at least partially rotary motion of the closure part. As a result, the device can be held and controlled by just one hand. A linkage is preferred as the gear.

It is particularly advantageous to have the closure part of the valve element be connected to a first lever, whereby a lever end of the first lever is designed as a first inclined plane with an angle of 20° to 45° and, opposite to said first inclined plane, a second inclined plane of a second lever is arranged, whereby the lever is connected to a manually operable trigger, whereby both inclined planes that are arranged opposite from each other engaged each other appropriately such that, upon a linear motion of the second lever by means of the trigger, the second inclined plane swivels the first inclined plane jointly with the first lever by at least 5° from the longitudinal axis of the device, whereby the closure part is rotated in the valve seat by the swiveling motion of the first lever.

It is also advantageous to have an elastic restoring element arranged on the first lever by means of which the first lever can be pushed back into its starting position after the swiveling motion of the first lever that is caused by the linear motion of the second inclined plane.

It is also advantageous to have an elastic restoring element arranged on the second lever that pushes the second lever back into the starting position after a manual linear motion proceeded.

BRIEF SUMMARY OF THE DRAWINGS

Further exemplary embodiments of the invention shall be illustrated in the following on the basis of eight schematic figures, though without limiting the scope of the invention. In the figures.

DETAILED DESCRIPTION OF THE DISCLOSURE

Figure 1:
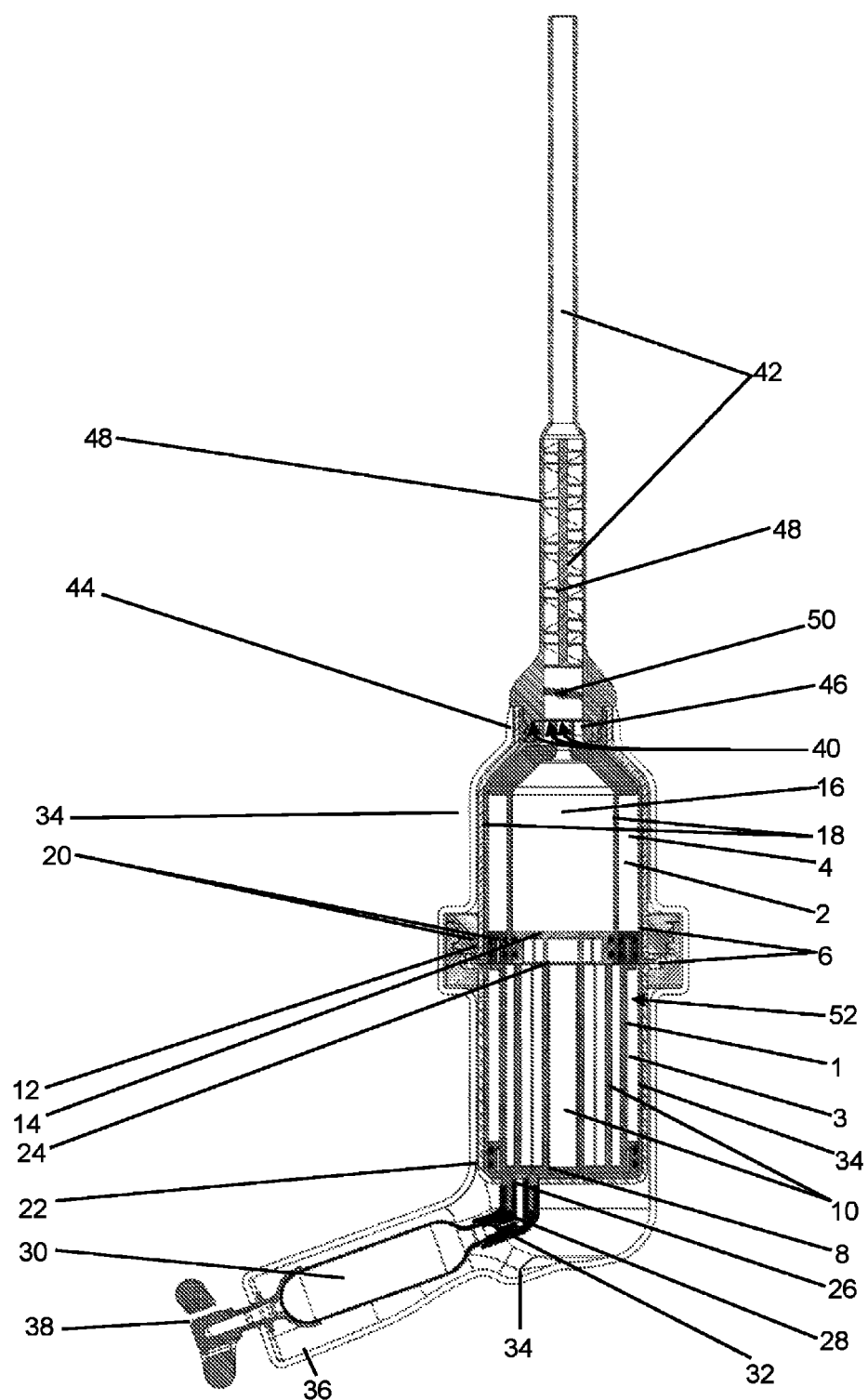
FIG. 1: shows a cross-sectional view of a paste application device according to the invention.
Figure 2:
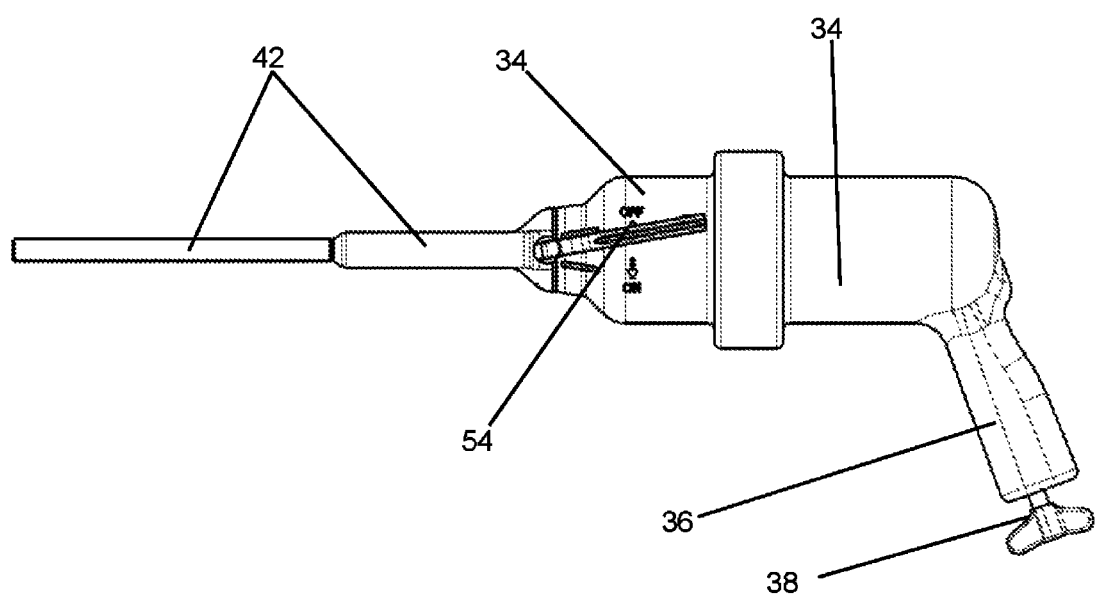
FIG. 2: shows a schematic side view of the paste application device according to FIG. 1.
Figure 3:
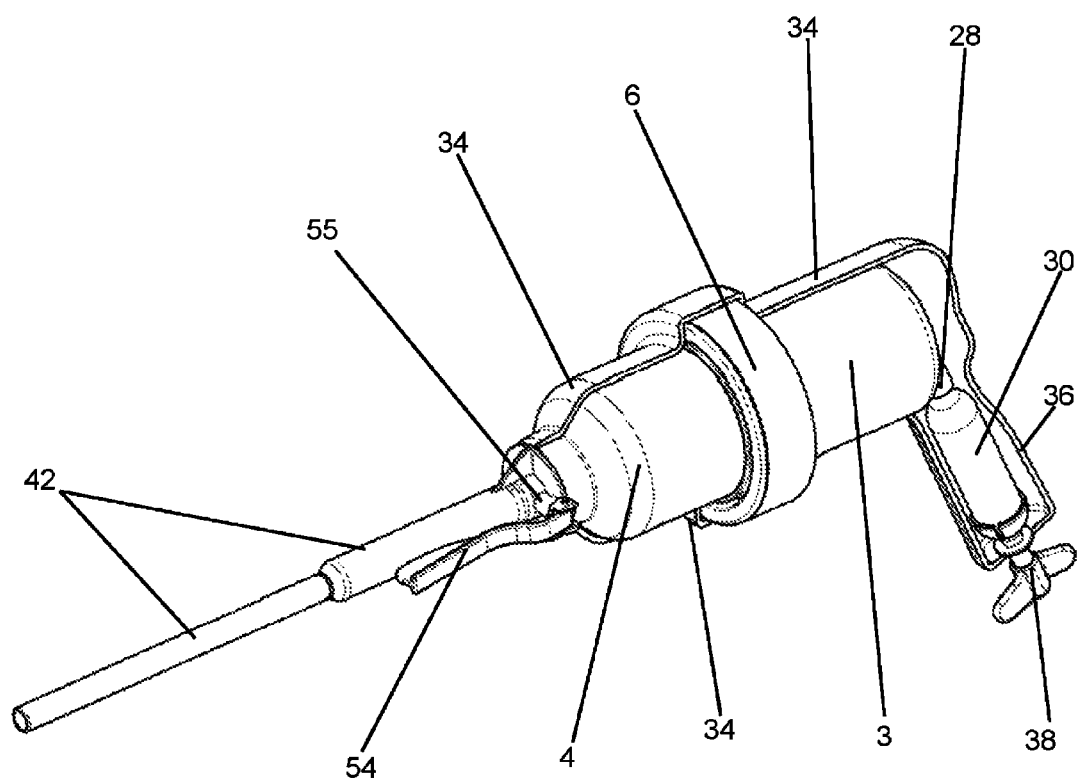
FIG. 3: shows a perspective view of the paste application device according to FIGS. 1 and 2 with the housing open.
Figure 4:
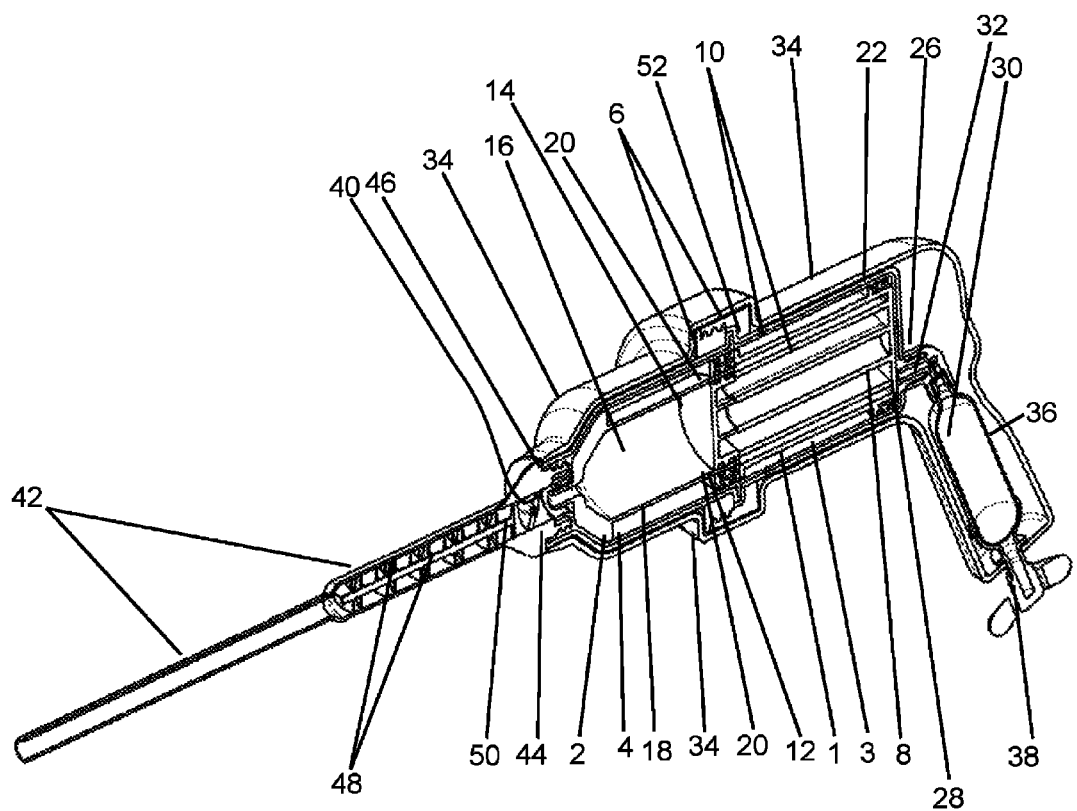
FIG. 4: shows a schematic perspective cross-sectional view of the paste application device according to FIGS. 1 to 3.

Identical or similar components are identified in the figures, to some extent, through the same reference numbers even if different paste application devices are concerned.

FIGS. 1 to 6 show different views of a compressed gas-driven paste application device according to the invention and/or parts thereof. The paste application device is designed in the way of a pistol and can be held in one hand and can be operated with the other hand. A hollow cylinder 1 made of plastic material and a two-component cartridge 2, arranged adjacent to the former, are situated on the inside of the paste application device. The hollow cylinder 1 is surrounded by a first part of a pressure vessel 3 and the two-component cartridge 2 is surrounded by a second part of a pressure vessel 4. The two parts of the pressure vessel 3, 4 consist of a metallic material, such as an aluminium alloy, zinc or steel, and are connected to each other in circumferential material-bonded manner on a circumferential outward-facing seam by means of a two-part union nut 6. The external walls of the hollow cylinder 1 and of the two-component cartridge 2 touch, by their surface against, the internal walls of the pressure vessel 3, 4 or are situated at a distance of maximally 100 μm to allow the pressure vessel 3, 4 to receive the forces acting on the walls of the hollow cylinder 1 and two-component cartridge 2 without any deformation of the walls that would disturb the function of the paste application device. The hollow cylinder 1, the two-component cartridge 2, and the pressure vessel 3, 4 have a cylindrical shape and/or an essentially cylindrical shape.

A plunger 8 is provided as working plunger on the inside of the hollow cylinder 1 and can be used to convert the energy stored in the compressed gas into a linear motion along the cylinder axis and/or in longitudinal direction of the paste application device. Two pestles 10 that are arranged coaxially with respect to each other and are oriented in the direction of the two-component cartridge 2 are arranged on the plunger 8. The pestles 10 can be used to drive two feed plungers 12, 14 that are arranged in the internal spaces 16, 18 of the two-component cartridge 2 that are arranged coaxially with respect to each other. The feed plungers 12, 14 are sealed with respect to the internal walls of the internal spaces 16, 18 by means of circumferential seals 20. Likewise, the plunger 8 touches in circumferential manner against the internal wall of the hollow cylinder 1 and is sealed in this place by means of circumferential seals 22.

Between the hollow cylinder 1 and the pestles 10 and the two-component cartridge 2, an aluminium composite foil 24 is taped onto the ends of the two-component cartridge 2 that are closed by the feed plungers 12, 14. The aluminium composite foil 24 is drawn in FIG. 1 only and is omitted from the other figures. This seals the content of the two-component cartridge 2. Specifically if volatile ingredients are present in the starting components and are stored in the internal spaces 16, 18 of the two-component cartridge 2, these ingredients are prevented from escaping and thus the starting components are prevented from changing during storage. The aluminium composite foil 24 is simply punctured when the feed plungers are propelled with the pestles 10 of the plunger 8.

The compressed gas exits through a connector 26 into the hollow cylinder 1, between the rear side of the plunger 8 and the closed side of the first part of the pressure vessel 3. For this purpose, the connector 26 projects through the soul opening in the otherwise closed base surface of the first part of the pressure vessel 3. The connector 26 and the hollow cylinder 1 are provided in the form of a single part. The connector 26 comprises an external thread onto which a connecting piece 28 made of plastic is screwed.

A compressed gas cartridge 30 is connected to the connecting piece 28 and can be opened by pushing the compressed gas cartridge 30 onto a hollow mandrel 32. As a result, the compressed gas cartridge 30 opens and the compressed gas can flow through the conduits in the connecting piece 28 and the connector 26 into the hollow cylinder 1, and can propel the plunger 8 in the direction of the two-component cartridge 2. The compressed gas cartridge 30 is preferred to be a liquid gas cartridge, in which, particularly preferably, carbon dioxide evaporates in order to provide the compressed gas.

The entire design specified thus far and/or all these parts (identified by reference numbers 1 to 32) are arranged inside a housing 34 made of plastic material. The housing 34 is provided, on the rear side (on the bottom in FIG. 1 and on the right in FIGS. 2, 3, and 4), in the form of a handle 36 and/or pistol handle 36 by means of which the paste application device can be held. The compressed gas cartridge 30 has on its bottom side an operating facility 38 attached to it that ends in a wing screw by means of which the compressed gas cartridge 30 can be screwed into the connecting piece 28 and can be opened by means of the hollow mandrel 32. Accordingly, the paste application device can be activated manually and/or made ready for use by operating the operating facility 38 and thus opening the compressed gas cartridge 30.

The front side of the cylindrical part of the two-component cartridge 2 and the coaxially arranged internal spaces 16, 18 situated inside converge conically and merge in dispensing openings 40 through which the starting components can be expelled from the internal spaces 16, 18 from the two-component cartridge 2. The starting components are mixed with each other downstream from the dispensing openings 40. In the storage state of the paste application device, the dispensing openings 40 are initially closed by a screw closure (not shown). In the application state, the closure is removed and a dispensing tube 42 is attached on the front face in its stead. For this purpose, an internal thread 44 is provided on the front face, in a socket on the two-component cartridge 2. An external thread 46 of the dispensing tube 42 is screwed into said internal thread 44. The closure (not shown) comprises an analogous external thread that was and/or can be screwed into the internal thread 44 of the two-component cartridge 2 in order to close the dispensing openings 40.

A static mixture 48 is provided on the inside of the dispensing tube 42 and can be used to mix the starting components when these flow through the dispensing tube 42. The flow through the dispensing tube 42 can be controlled by means of a manually operable flap valve 50 that is supported in the channel of the dispensing tube 42 such that it can rotate. When the flap valve 50 is closed, the starting components can no longer be expelled from the two-component cartridge 2 and, accordingly, the feed plungers 12, 14 and the plunger 8 cannot be propelled any further. By not interrupting the gas flow, unlike with other application devices known from the prior art, there cannot be any further expansion of already supplied gas and no ensuing undesired continuation of the flow of the paste mixture. Arranging the flap about 50 in the channel of the dispensing tube 42 is expedient, since the load on the bearings of the flap valve 50 is limited due to the small cross-section.

Multiple ventilation openings 52 are provided one above the other in the hollow cylinder 1 and the first part of the pressure vessel 3. The ventilation openings 52 are arranged at a level of the hollow cylinder 1 that corresponds at least, and preferably, to approximately the level of the plunger 8 such that, upon the plunger 8 being propelled in the direction of the two-component cartridge 2 to the limit stop, the region between the plunger 8 and the rear side of the hollow cylinder 1 is opened with respect to the surroundings by means of the ventilation openings 52 and the pressure remaining can escape into the surroundings. This ensures that the spent paste application device is no longer pressurised during recycling or disposal and can therefore be processed without any risk.

The flap valve 50 can be operated from outside of the paste application device through an operating element 54 (shown in FIGS. 2 and 3) in the form of a lever 54 being connected to the flap valve 50 such that the flap valve 50 can be rotated in the dispensing tube 42 by the lever 54 such that the flow of the starting components and mixture can be controlled. For this purpose, the axle (not shown in FIGS. 2 and 3) of the flap valve 50 is supported in a bearing 55 and/or a sleeve 55 through which the axle is guided such that the position of the flap valve 50 can be set by rotating the axle by means of the lever 54.

Figure 5:
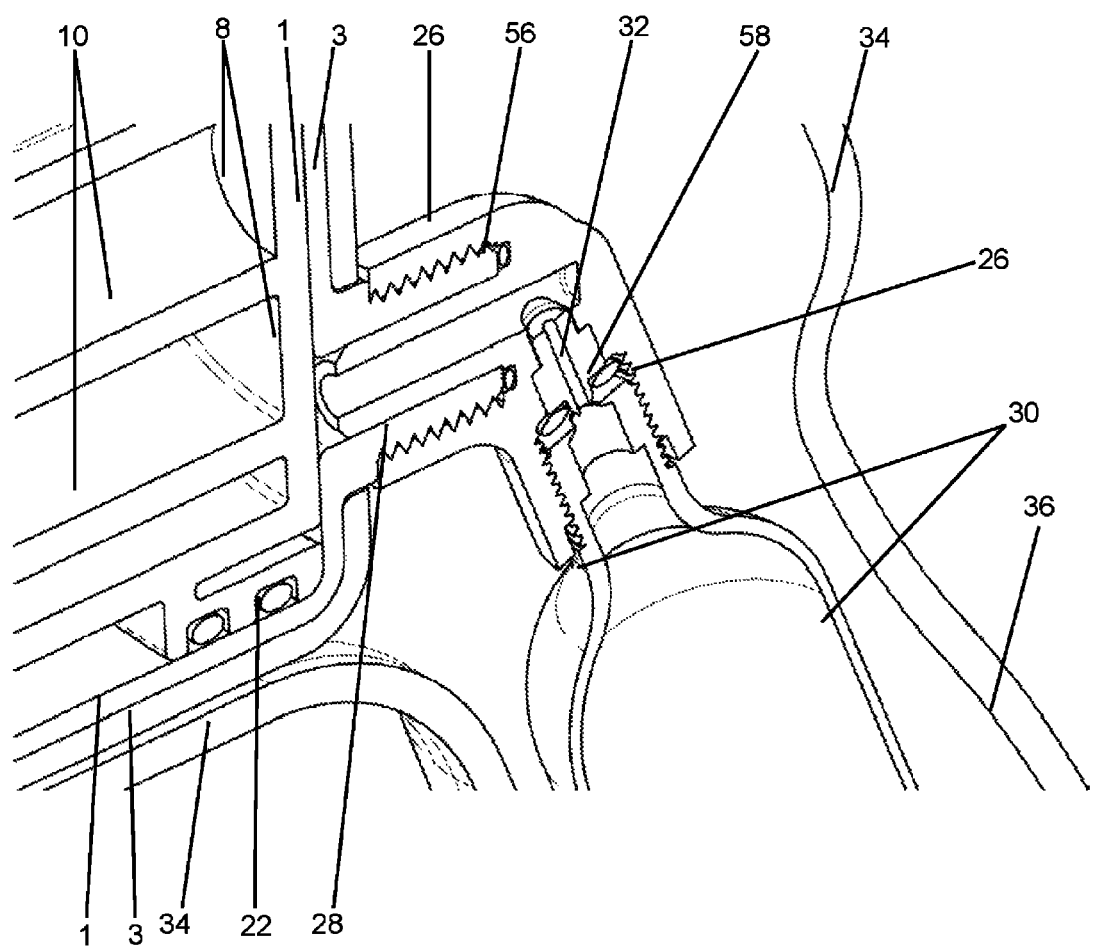
FIG. 5: shows a magnified partial view of the connector for the gas cartridge of the paste application device according to FIG. 4.

As is shown and in the magnified partial view according to FIG. 5 and is well-visualised, an external thread is provided on the connector 26 onto which the connecting piece 28 is screwed by means of an internal thread. A seal 56 is provided in order to seal the two parts 26, 28 with respect to each other in pressure-tight manner. Analogously, a seal 58 is provided between the connecting piece 28 and the compressed gas cartridge 30 and/or between the hollow mandrel 32 and the compressed gas cartridge 30.

Figure 6:
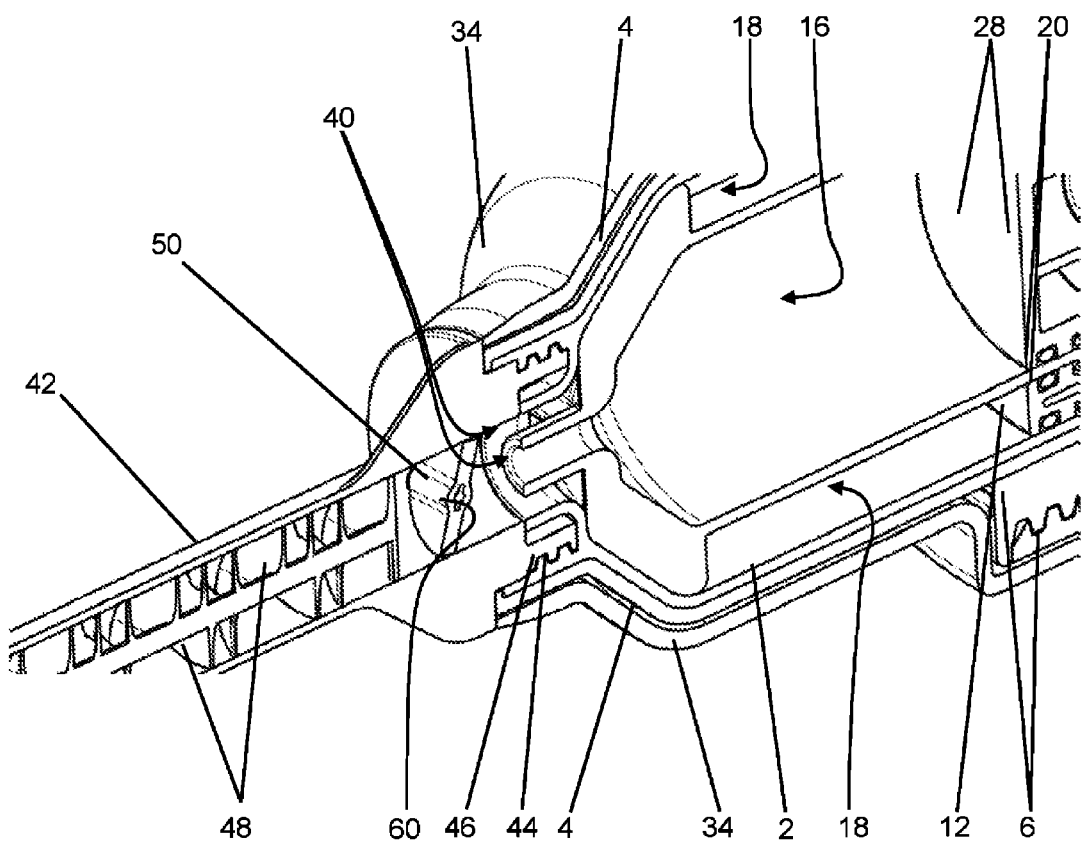
FIG. 6: shows a magnified partial view of the valve element for the gas cartridge of the paste application device according to FIG. 4.

It is well-visualised in the magnified partial view according to FIG. 6 that the flap valve 50 comprises a steel axle 60 about which the flap valve 50 can be rotated in the dispensing tube 42 by means of the operating element 54. The steel axle 60 provides the needed stability of the flap valve 50. The steel axle 60 must not be subject to plastic deformation under the effect of the pressure from the compressed gas cartridge 30, mediated by the starting components, to the extent that the function of the flap valve 50, for example the mobility of the flap valve 50, would no longer be ensured. Rotating the flap valve 50 about the steel axle 60 allows the volume flow through the dispensing tube 42 to be controlled, while the gas pressure mediated by the plunger 8 and the feed plungers 12, 14 expel the content from the two-component cartridge 2, i.e. expel the starting components from the two-component cartridge 2.

Figure 7:
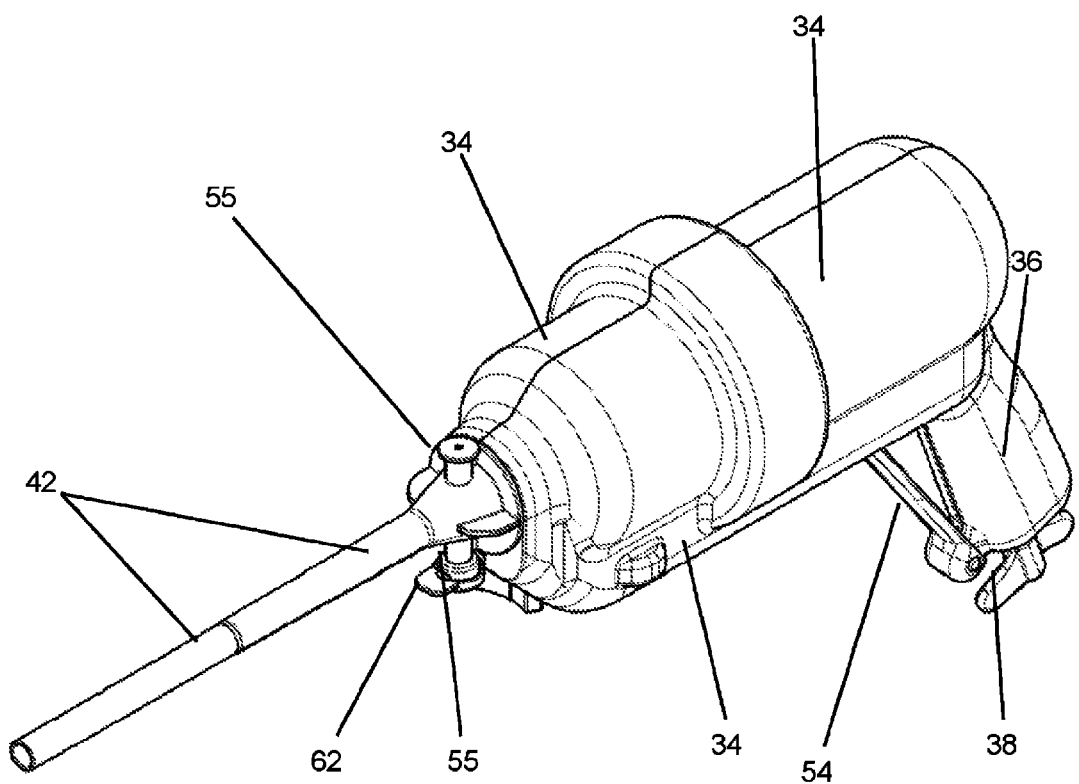
FIG. 7: shows a perspective view of an alternative paste application device that has a different operating facility for the valve element.
Figure 8:
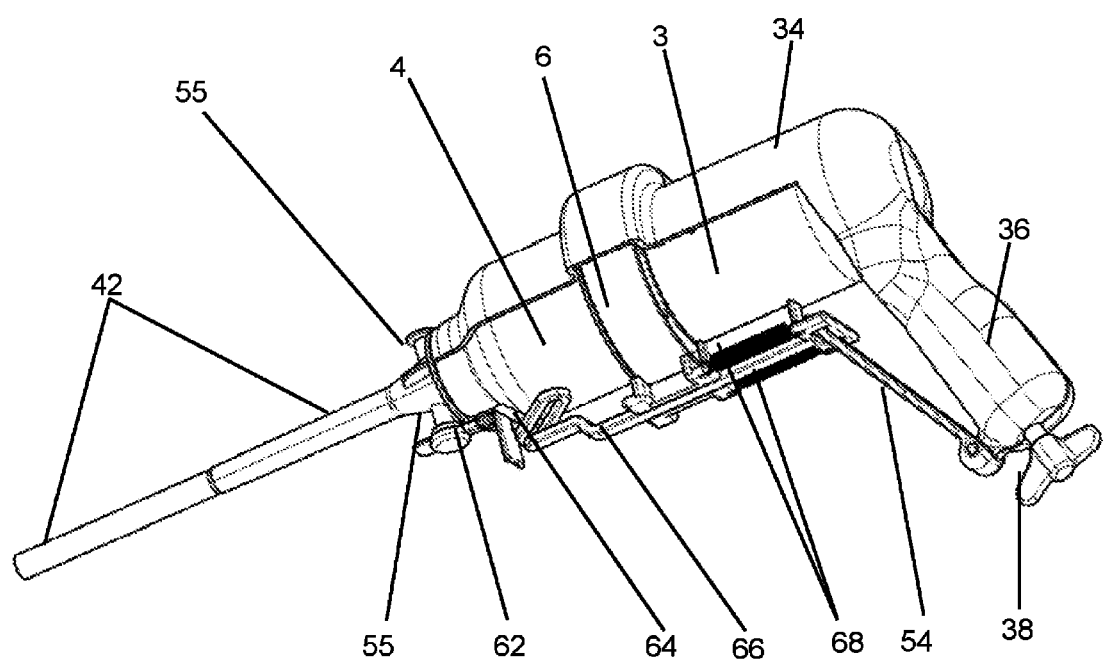
FIG. 8: shows a perspective view of the paste application device according to FIG. 7 with the housing open.

FIG. 7 shows a perspective view of an alternative paste application device having a different operating facility for the valve element (not shown in FIGS. 7 and 8) and FIG. 8 shows a perspective view of the paste application device according to FIG. 7 with the housing 34 open. The design of said paste application device is the same as the one according to FIGS. 1 to 6 except for the bearing of the valve element and the functional principle of the operating facility being different. In the present embodiment, the valve element is also implemented by means of a flap valve, whereby the rotary axle (made of steel) is rotated by 90° with respect to the cylinder symmetry axis of the two-component cartridge as compared to the arrangement according to FIGS. 1 to 6. The rotary axle is supported in two sleeve-shaped bearings 55 one of which comprises a through-going bushing for the rotary axle, whereby the rotary axle is attached to a rod 62 by means of which the rotary axle can be rotated from outside.

The rod 62 is connected to a rail 64 that is connected to the housing 34 by means of an axle such that it can be rotated. A cylinder that is attached to a second rod 66 runs in said rail 64. The second rod 66 is connected, by means of a hinge, to an operating element 54 that is attached in tiltable manner on the pistol handle 36 of the paste application device. Two tension springs 68 are attached as restoring elements on the second rod 64 and on a bracket on the housing 34 and can be used to restore the operating element 54 and/or the trigger 54 into the starting position when no force is exerted any longer on the operating element 54.

In this embodiment, the operating facility for the rotatable flap valve comprises the operating element 54, the rods 62, 66, the rail 66, the springs 68, and all fastening means that serve for supporting these parts on the housing 34.

Due to this design, the entire paste application device can be held and operated with one hand. It is self-evident that other configurations are conceivable as well by means of which said one-handed operability can be made feasible.

The features of the invention disclosed in the preceding description and in the claims, figures, and exemplary embodiments, can be essential for the implementation of the various embodiments of the invention both alone and in any combination.

LIST OF REFERENCE NUMBERS

1 Hollow cylinder
2 Two-component cartridge
3 Pressure vessel, first part
4 Pressure vessel, second part
6 Union nut
8 Plunger
10 Pestle
12 Feed plunger
14 Feed plunger
16 Inner internal space
18 Outer internal space
20 Seal
22 Seal
24 Aluminium composite foil
26 Compressed gas connector
28 Connecting piece
30 Compressed gas cartridge
32 Puncturing mandrel/hollow mandrel
34 Housing
36 Handle
38 Operating facility
40 Dispensing opening
42 Dispensing tube
44 Internal thread
46 External thread
48 Static mixer
50 Rotatable flap valve
52 Ventilation opening
54 Operating element
55 Bearing/sleeve
56 Seal
58 Seal
60 Steel axle
62 Rod
64 Rail
66 Rod
68 Tension spring

The invention claimed is:

1. A paste application device for storage of at least two starting components, for mixing the at least two starting components to form a paste, and for the application of the paste, the device comprising:
    a two-component cartridge comprising two cylindrical internal spaces, two feed plungers that can be shifted axially in the internal spaces and limit the internal spaces on a first side of the two-component cartridge, and at least two dispensing openings by means of which the internal spaces are open on a second side of the two-component cartridge that is opposite from the first side;
    a hollow cylinder made of a plastic material and having one front face that is open and another front face that is partially closed, in which is situated an axially mobile plunger that has two pestles attached to it, wherein the pestles are oriented in the direction of the open front face, wherein the open front face of the hollow cylinder is arranged to axially contact against the first side of the two-component cartridge, and wherein the plunger closes in gas-tight manner against the internal walls of the hollow cylinder,
    wherein the two-component cartridge and the hollow cylinder are arranged in a pressure vessel made of metal, a high-strength plastic material or a fibre-reinforced plastic material, wherein the pressure vessel touches against the hollow cylinder or is situated at a distance from the hollow cylinder of at most 0.1 mm,
    wherein the hollow cylinder comprises, on the front face that is partially closed, a connector for a compressed gas cartridge that extends through an opening in the pressure vessel, and
    further wherein a manually operable valve element is attached downstream from the dispensing openings or a dispensing tube having a manually operable valve element attached downstream from the dispensing openings, wherein the valve element attached downstream from the dispensing openings is usable to regulate the volume flow of the starting components through the dispensing openings.

2. The paste application device according to claim 1, wherein the valve element is arranged in a conduit that is formed by a dispensing tube, wherein a static mixture is provided in the dispensing tube by means of which the starting components are mixable while flowing through the mixer.

3. The paste application device according to claim 1, wherein the pressure vessel has a two-part design, whereby two parts are connected to each other in force-locking manner by riveting, by a screw connection and/or by a union nut, wherein a first part of the two parts of the pressure vessel contains the two-component cartridge and the second part of the two parts of the pressure vessel contains the hollow cylinder.

4. The paste application device according to claim 1, wherein the two-component cartridge, or at least regions thereof, is a coaxial cartridge, wherein one of the internal spaces in the coaxial cartridge is cylindrical and situated inside and the other internal space is cylindrical and coaxially surrounds the inner internal space.

5. The paste application device according to claim 1, further comprising a closure for closing the dispensing openings that is fastenable by a first thread of the closure to an opposite second thread of the dispensing openings, wherein the dispensing tube comprises a corresponding external thread that is fastenable to the opposite second thread.

6. The paste application device according to claim 5, wherein the closure is a key for opening a compressed gas cartridge and for connecting the compressed gas cartridge to the connector of the hollow cylinder, wherein the closure is pluggable, on the floor-side, onto the compressed gas cartridge as a key thus rendering the compressed gas cartridge rotatable and/or shiftable in longitudinal direction for opening the compressed gas cartridge and for connecting the compressed gas cartridge to the connector of the hollow cylinder.

7. The paste application device according to claim 1, further comprising:
   an internal thread provided on the connector of the hollow cylinder by means of which the compressed gas cartridge is attachable to the connector in pressure-tight manner; and/or a puncturing mandrel for opening of the compressed gas cartridge on the connector of the hollow cylinder.

8. The paste application device according to claim 1, further comprising: a protective foil/film arranged between the hollow cylinder and the two-component cartridge and the protective foil/film closes the internal spaces of the two-component cartridge on the first side, wherein the protective foil/film is pasted, welded or bonded onto the two-component cartridge.

9. The paste application device according to claim 1, wherein the pressure vessel consists of aluminium, zinc, an aluminium alloy and a steel.

10. The paste application device according to claim 1, wherein the valve element is operable from outside by means of a lever on the dispensing tube or a trigger on a handle of the paste application device.

11. The paste application device according to claim 1, wherein at least one through-going ventilation opening is provided in the external wall of the hollow cylinder facing in the direction of the two-component cartridge and in the wall of the pressure vessel such that the pressure escapes from the hollow cylinder when the plunger is arranged between the ventilation opening and the two-component cartridge.

12. The paste application device according to claim 1, wherein the two-component cartridge, the hollow cylinder, and the pressure vessel are arranged in a housing, wherein a pressure gas cartridge is arranged in the housing.

13. The paste application device according to claim 1, wherein the distances between the pressure vessel and the external wall of the two-component cartridge and between the pressure vessel and the external wall of the hollow cylinder are less than 100 µm.

14. The paste application device according to claim 1, wherein the paste application device is holdable by one hand and the valve element is operable by the same hand.

15. A method for mixing and dispensing a paste, the method comprising:
   providing the paste application device according to claim 1;
   conducting a compressed gas from a compressed gas cartridge through the connector of the hollow cylinder into the hollow cylinder, wherein the pressure vessel receives the force of the compressed gas acting on the internal walls of the hollow cylinder and the axially mobile plunger with the two pestles is propelled by the compressed gas in the hollow cylinder in the direction of the two-component cartridge;
   driving the feed plungers forward into the at least two internal spaces of the two-component cartridge via the propelled pestles of the plunger, wherein the starting components are expelled from the internal spaces of the two-component cartridge through the at least two dispensing openings of the internal spaces;
   stopping the flow of the starting components by a closed valve element downstream of the dispensing openings as seen in flow direction and a manual operation of an operating element opens the closed valve element such that the starting components, and/or the mixture thereof, flow through the opened valve element and, after the starting components are mixed, the mixture is applicable.

16. The method according to claim 15, wherein, in the absence of a manual force acting on the operating element, the valve element is closed by the action of a force of a restoring element.

17. The method according to claim 15, wherein a closure is removed from the paste application device before conducting the compressed gas into it, and the closure close the dispensing openings of the internal spaces of the two-component cartridge, and a dispensing tube is being attached in front of the dispensing openings of the internal spaces, in which the valve element is arranged, wherein the compressed gas cartridge is opened after attaching the dispensing tube and the compressed gas is conducted into the hollow cylinder upon the compressed gas cartridge being opened.

18. The paste application device according to claim 13, wherein the distances between the pressure vessel and the external wall of the two-component cartridge and between the pressure vessel and the external wall of the hollow cylinder are less than 50 µm.

19. The method according to claim 16, wherein the restoring element is an elastic spring.

* * * * *